United States Patent [19]

Goddin, Jr. et al.

[11] Patent Number: 4,557,911

[45] Date of Patent: Dec. 10, 1985

[54] PROCESS FOR PRODUCING SWEET $CO_2$ AND HYDROCARBON STREAMS

[75] Inventors: Clifton S. Goddin, Jr.; Boyd E. Cabanaw, both of Tulsa, Okla.

[73] Assignee: Amoco Corporation, Chicago, Ill.

[21] Appl. No.: 625,490

[22] Filed: Jun. 28, 1984

[51] Int. Cl.$^4$ .................. C01B 17/16; C01B 31/20
[52] U.S. Cl. ................................ 423/228; 423/220
[58] Field of Search .................. 423/220, 228, 229

[56] References Cited

U.S. PATENT DOCUMENTS

| | | | |
|---|---|---|---|
| 3,275,403 | 9/1966 | Mayland | 423/229 |
| 3,961,015 | 6/1976 | Dailey | 423/229 |
| 4,079,117 | 3/1978 | Butwell | 423/228 |
| 4,217,236 | 8/1980 | Sartori et al. | 252/189 |
| 4,241,032 | 12/1980 | Werner et al. | 423/226 |
| 4,289,738 | 9/1981 | Pearce et al. | 423/228 |
| 4,356,161 | 10/1982 | McNamara et al. | 423/573 R |
| 4,405,581 | 9/1983 | Savage et al. | 423/226 |
| 4,406,868 | 9/1983 | Carter et al. | 423/228 |
| 4,466,946 | 8/1984 | Goddin, Jr. et al. | 423/228 |

FOREIGN PATENT DOCUMENTS

1520277 4/1968 France ........................ 423/229

Primary Examiner—H. T. Carter

[57] ABSTRACT

In a preferred embodiment, carbon dioxide and hydrogen sulfide are removed from a gaseous stream also containing a recoverable hydrocarbon product by $CO_2$ sweetening, bulk $CO_2$ removal, and hydrocarbon sweetening absorption steps, each absorption utilizing the same alkanolamine as absorbent. According to another aspect, each amine can be selected from the group consisting of tertiary amines and sterically hindered amines. According to yet another aspect, a feed gas comprising hydrogen sulfide and carbon dioxide can be introduced successively into a carbon dioxide sweetening absorption zone, then into a bulk $CO_2$ removal absorption zone, then into a hydrocarbon sweetening absorption zone. Alternatively, a feed gas comprising hydrogen sulfide and carbon dioxide can be introduced first into a bulk $CO_2$ removal absorption zone and then streams from the bulk $CO_2$ removal zone can be provided respectively to the hydrocarbon sweetening absorption zone and the $CO_2$ sweetening absorption zone.

11 Claims, 4 Drawing Figures

PROCESS FOR PRODUCING SWEET $CO_2$ AND HYDROCARBON STREAMS

FIELD OF THE INVENTION

The invention relates to gas processing. In a particular aspect, the invention relates to processing gaseous streams comprising hydrocarbons, carbon dioxide ($CO_2$) and hydrogen sulfide ($H_2S$) and producing sweet $CO_2$ and hydrocarbon product streams.

BACKGROUND OF THE INVENTION

Naturally occurring low quality sour gas reservoirs exist which contain, in addition to methane and other hydrocarbons, significant quantities of carbon dioxide and hydrogen sulfide. Such reservoirs have sometimes not been produced because of the expense of recovering hydrocarbon and other stream(s) meeting sales specifications and environmental requirements. Developments in recent years include carbon dioxide miscible flooding to facilitate enhanced oil recovery from certain reservoirs. Such carbon dioxide miscible flooding requires sources of large quantities of carbon dioxide, and if the carbon dioxide is to be transported over significant distances, the carbon dioxide should be substantially free of hydrogen sulfide to meet environmental regulations. Accordingly, efficient and economical processes for producing sweet high purity carbon dioxide and hydrocarbon streams meeting sales specifications and environmental requirements from such naturally occurring low quality sour natural gas reservoirs are highly desirable.

In addition, during the production of a reservoir by carbon dioxide miscible flooding it is known that after a time carbon dioxide breakthrough occurs, i.e., carbon dioxide appears in the produced fluids in significant quantities. Gaseous streams derived, for example, from wellhead separator(s) of such carbon dioxide miscible flood produced reservoirs can, therefore, have compositions similar to gas produced from naturally occurring low quality reservoirs, for example, high levels of carbon dioxide and significant amounts of hydrogen sulfide and hydrocarbons.

Typically, processing the above gases can involve sulfur recovery, usually by the Claus reaction. When the acid gas feed stream to the sulfur recovery facility contains 10 to 15 mol percent $H_2S$ or greater, the sulfur recovery can be carried out using Claus technology involving a furnace and/or one or more Claus reactors. For example, for acid gas feeds containing 40 to 50 mol percent $H_2S$ or greater, a straight through design Claus plant can be utilized; and, for feeds containing 40 to 50 mol percent $H_2S$ down to about 10 to 15 mol percent $H_2S$, a split flow design Claus plant can be utilized. When the gaseous feeds are leaner in $H_2S$, however, specialized designs must be utilized. Accordingly it is desirable in design of gas processing facilities to provide a Claus plant feed having greater than 10 to 15 mol percent $H_2S$, thereby avoiding the use of the less efficient specialized designs.

Consequently, there is a continuing need for processes for treating gaseous streams containing significant quantities of $CO_2$ and $H_2S$, in addition to hydrocarbons, which can economically produce sweet $CO_2$ and hydrocarbon product streams and concentrate $H_2S$ for feed to a sulfur recovery plant.

SUMMARY OF THE INVENTION

According to the invention, there is provided a process for removing hydrogen sulfide and carbon dioxide from a gaseous feedstream which also comprises hydrocarbons and for producing a sweet $CO_2$ stream, a sweet sales-quality hydrocarbon product stream, and an acid gas stream enriched in $H_2S$ suitable as feed for a sulfur recovery facility.

According to one embodiment of the invention, the gaseous feed stream can be introduced into a $CO_2$ sweetening absorption zone and contacted with a first aqueous alkanolamine solution stream under conditions effective for selectively removing hydrogen sulfide relative to carbon dioxide and for absorbing at least a major portion of the hydrogen sulfide from the gaseous stream, producing a first gaseous product stream and a first rich amine stream containing selectively absorbed hydrogen sulfide. The first gaseous product stream can then be introduced into a bulk $CO_2$ removal absorption zone and contacted with a second aqueous alkanolamine solution stream under conditions effective for absorbing and removing a major portion of carbon dioxide therefrom, producing a second gaseous product stream and a second rich amine stream containing the thus absorbed carbon dioxide. The second gaseous product stream can then be introduced into a hydrocarbon sweetening absorption zone and contacted with a third aqueous alkanolamine solution stream under conditions effective for selective removal of substantially all remaining hydrogen sulfide, and sufficient carbon dioxide to meet sales specifications, producing a third sweet gaseous product stream and a third rich amine stream.

In a further aspect of this embodiment of the invention, each of the first aqueous alkanolamine solution stream and the third aqueous alkanolamine solution stream comprises a substantially identical tertiary or a sterically hindered amine effective for selective $H_2S$ removal such as, for example, methyldiethanolamine (MDEA) or diisopropanolamine (DIPA), solution.

In yet a further aspect of this embodiment of the invention, the first rich amine stream and the third rich amine stream can be introduced into a first regeneration zone and absorbed carbon dioxide and hydrogen sulfide removed therefrom, producing the first lean aqueous alkanolamine solution stream and the third lean aqueous alkanolamine solution stream. The second rich amine stream can be introduced into a second regeneration zone and absorbed acid gases removed therefrom producing a $CO_2$ product stream lean in hydrogen sulfide and the second lean (or semilean) aqueous alkanolamine stream.

In yet a further aspect of this embodiment of the invention, each of the first, the second, and the third aqueous alkanolamine streams comprises a substantially identical tertiary or sterically hindered amine solution.

According to a second embodiment of the invention, the gaseous feedstream can be introduced into a bulk $CO_2$ removal absorption zone and contacted therein with a first aqueous alkanolamine solution stream under conditions effective for absorbing and removing a major portion of carbon dioxide, and at least a first portion of hydrogen sulfide from the gaseous stream, producing a first gaseous product stream and a first rich amine stream containing absorbed carbon dioxide and hydrogen sulfide. The first gaseous product stream can then be introduced into a hydrocarbon sweetening absorption zone and contacted therein with a second aqueous alkanolamine solution stream under conditions effective for removal of a major portion of the remaining hydrogen sulfide, producing a second (sweet) gaseous product stream comprising hydrocarbons and a second rich amine stream. Carbon dioxide and hydrogen sulfide absorbed in the first rich amine stream and the second rich amine stream can be removed by regeneration, producing an acid gas stream containing such removed carbon dioxide and hydrogen sulfide. The acid gas stream can then be introduced into a $CO_2$ sweetening absorption zone and contacted therein with a third aqueous alkanolamine solution stream under conditions selective for the removal of hydrogen sulfide relative to carbon dioxide, producing a second gaseous product stream comprising predominantly sweet carbon dioxide and a third rich amine stream containing absorbed hydrogen sulfide.

According to a further aspect of this embodiment of the invention, the first aqueous alkanolamine solution, the second aqueous alkanolamine solution, and the third aqueous alkanolamine solution, each comprises an alkanolamine selected from the group consisting of tertiary amines and sterically hindered amines effective for selective removal of hydrogen sulfide relative to carbon dioxide such as, for example, methyldiethanolamine.

According to the further aspect of this embodiment of the invention, the first rich amine stream can be introduced into a first regeneration zone and carbon dioxide and hydrogen sulfide removed therefrom, producing a first acid gas stream, and a first semilean alkanolamine solution stream which can be returned to the bulk $CO_2$ removal absorption zone. A portion of the first semilean alkanolamine solution stream can then be introduced into a second regeneration zone and a substantial portion of the remaining absorbed acid gas can be removed therefrom to produce a second acid gas stream and the second lean aqueous alkanolamine solution stream which can be returned to the hydrocarbon sweetening and the $CO_2$ sweetening absorption zones. The first acid gas stream can then be provided to the $CO_2$ sweetening absorption zone. The second acid gas stream can be provided directly to a Claus sulfur recovery unit or provided to a Pre-Claus selective $H_2S$ removal zone.

BRIEF DESCRIPTION OF THE DRAWINGS

The invention will be further understood and appreciated from the following detailed description and the drawings in which.

DETAILED DESCRIPTION OF THE INVENTION

According to the invented process, $H_2S$ and $CO_2$ can be removed by absorption from gaseous streams comprising $H_2S$, $CO_2$, and hydrocarbons such as methane, ethane, and the like. The gaseous stream can be, for example, $CO_2$ miscible flood produced gas, or naturally occurring low quality sour natural gas, and comparable streams, and can contain broadly from about 10 to about 90 mol% $CO_2$, and from about 0.1 to about 20 mol% $H_2S$.

According to a first embodiment of the invention, removal of $H_2S$ and $CO_2$ from the gaseous feed stream can proceed according to the invention in the following sequence of absorption steps: (1) $CO_2$ sweetening, (2) bulk $CO_2$ removal, and (3) hydrocarbon sweetening. A sweet $CO_2$ stream is produced in accordance with this embodiment of the invention by regenerating laden alkanolamine solution from Step (2) and an acid gas stream can be produced by regenerating laden alkanolamine solutions from Step (1) and Step (3).

Figure 1:
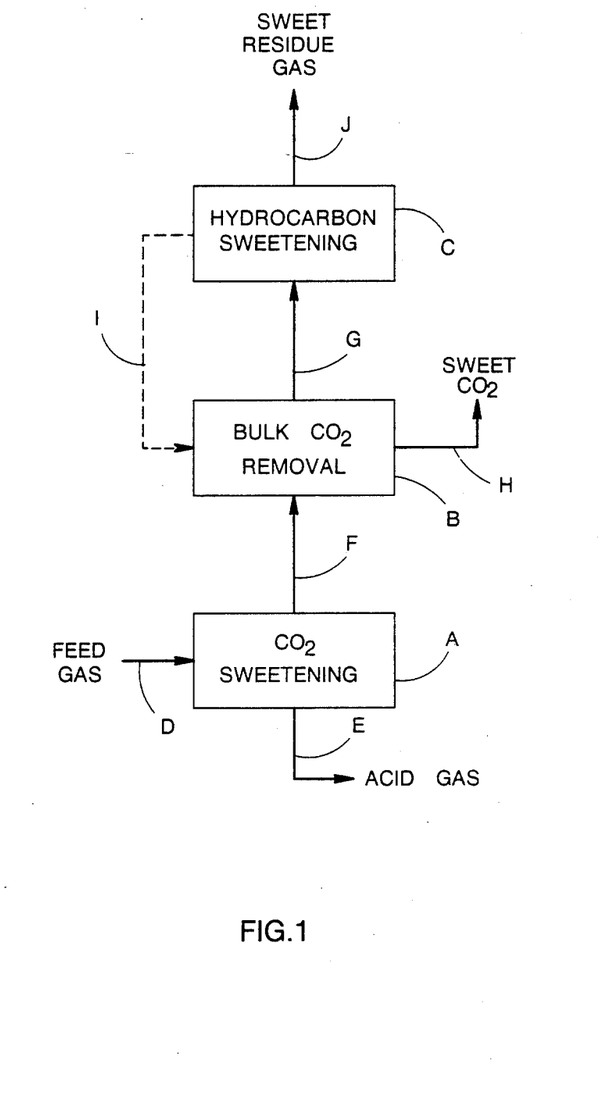
FIG. 1 represents a block diagram of a first embodiment of the invention.

Thus, referring to FIG. 1, a gaseous feedstream comprising $H_2S$, $CO_2$, and hydrocarbons can be introduced by Line D into $CO_2$ Sweetening Zone A. An acid gas stream comprising $H_2S$ and $CO_2$ can be removed by Line E, for example, to a Claus Plant (not shown) for the recovery of sulfur. A gaseous product stream comprising hydrocarbons, $CO_2$, and less than a predetermined allowable amount of $H_2S$, for example, less than 100 ppm $H_2S$ in the $CO_2$, can be removed from Zone A by Line F and introduced into Bulk $CO_2$ Removal Zone B. A major portion of the $CO_2$ in Line F is removed from the hydrocarbons in Zone B and can be removed as a sweet $CO_2$ stream in Line H, containing less than a predetermined allowable amount of $H_2S$, for example, less than about 100 ppm $H_2S$. A hydrocarbon stream greatly reduced in $CO_2$ content can be removed from Zone B by Line G and introduced into Hydrocarbon Sweetening Zone C. In Hydrocarbon Sweetening Zone C, further removal of $CO_2$ and $H_2S$ to below predetermined allowable limits, for example, to below 2 mol percent $CO_2$ and to below 4 ppm $H_2S$, can occur producing, for example, a sales quality hydrocarbon residue gas product stream which can be removed by Line J. The rich amine stream from Zone C partly laden with $H_2S$ and $CO_2$ can, if desired, be returned to the Bulk $CO_2$ Removal Zone for further absorption of $CO_2$ as indicated by dashed line I.

According to a second embodiment of the invention, removal of $H_2S$ and $CO_2$ from the gaseous feed stream can proceed according to the following sequence of absorption steps: (1) bulk $CO_2$ removal (2) hydrocarbon sweetening of the gaseous product from step (1), and (3) sweetening of the sour $CO_2$ stream produced by regeneration of laden alkanolamine solution streams from Steps (1) and (2).

Figure 2:
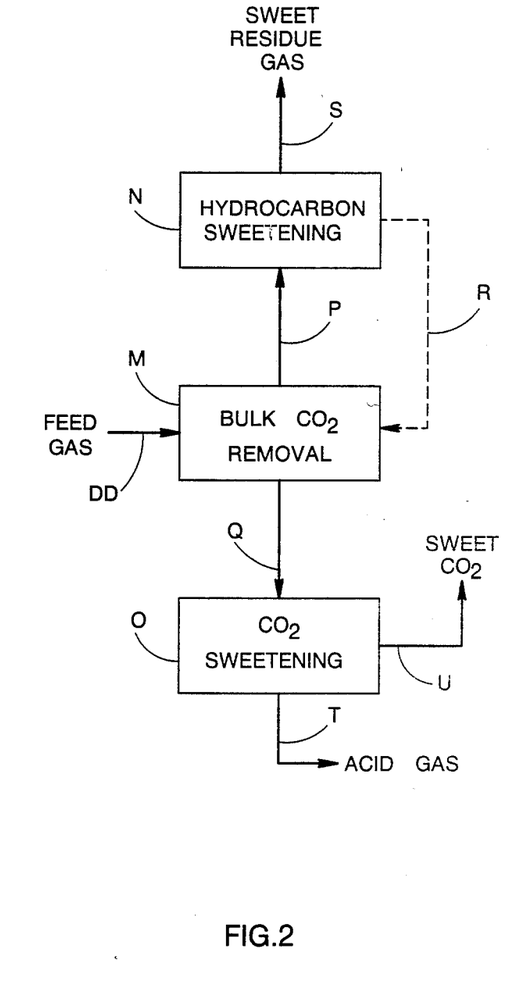
FIG. 2 represents a block diagram of a second embodiment of the invention.

Thus, referring to FIG. 2, a gaseous feedstream comprising $H_2S$, $CO_2$, and hydrocarbons can be introduced by Line DD into Bulk $CO_2$ Removal Zone M. A major portion of the $CO_2$, as well as of the $H_2S$, is separated from the hydrocarbons in Zone M and can be removed as a sour $CO_2$ stream in Line Q to $CO_2$ Sweetening Zone O discussed below. A hydrocarbon stream greatly reduced in $CO_2$ content can be removed from Zone M by Line P and introduced into Hydrocarbon Sweetening Zone N. In Zone N, further removal of $CO_2$ and $H_2S$ to below predetermined allowable limits, for example, to below 2 mol percent $CO_2$ and below 4 ppm $H_2S$ can occur producing, for example, a sales quality hydrocarbon sweet residue gas product stream which can be removed by Line S. A rich amine stream partly laden with $H_2S$ and $CO_2$ can, if desired, be returned to the Bulk $CO_2$ Removal Zone M for further absorption of acid gases, as indicated by dashed line R. In $CO_2$ Sweetening Zone O, a sweet $CO_2$ stream having less than a predetermined allowable amount of $H_2S$ can be produced and removed by Line U. An acid gas stream comprising $H_2S$ and $CO_2$ can be removed by Line T.

In addition, it will be appreciated that further stages of selective $H_2S$ removal can, if desired, be utilized for further treatment of the acid gas stream to produce an acid gas feed enriched in $H_2S$ suitable as feed to a sulfur recovery facility. The invented process when applied, for example, to $CO_2$ miscible flood produced gases or to low quality sour natural gas, can be used to produce a residue (hydrocarbon) gas meeting pipeline specifications for $H_2S$ and $CO_2$, typically less than about 4 ppm $H_2S$ and less than about 2 mol% $CO_2$, a sweet $CO_2$ product gas containing less than, for example, about 100 ppm $H_2S$, and, according to a preferred embodiment, an acid gas stream suitable as feed to a Claus plant containing not less than about 10 to 15 mol% $H_2S$.

According to a preferred aspect of the invention, the same aqueous alkanolamine solution is utilized in the bulk $CO_2$ removal zone, the hydrocarbon sweetening zone, and the $CO_2$ sweetening zone, and comprises a single amine or a single amine mixture of amines selected from the group consisting of tertiary amines such as triethanolamine (TEA), methyldiethanolamine (MDEA) and the like, and sterically hindered amines effective for selective removal of $H_2S$ relative to carbon dioxide, such as, for example, DIPA. By using a single alkanolamine or a single mixture of alkanolamines, operation of the invented process is simplified as compared with alternative processes, for example, the alkanolamine regeneration facilities can be consolidated, and cross contamination of alkanolamine streams is virtually eliminated.

The alkanolamine solution according to the invention can have a concentration of amine about 1 to 7 moles per liter of the total solution, and preferably from about 2 to 5 moles per liter, depending primarily on the specific amine employed.

The alkanolamine solution according to the invention can include a variety of additives typically employed in amine solution gas removal processes, e.g., antifoaming agents, antioxidants, corrosion inhibitors, and the like. The amount of these additives will typically be in the range that they are effective, i.e., an effective amount. Also, the amines described herein may be admixed with other amines as a blend.

In the $CO_2$ sweetening absorption zone of the invention, the gaseous feed stream or the sour $CO_2$ gas stream can be contacted with an alkanolamine solution according to the invention and at least a major portion of the $H_2S$ can be removed from the gaseous stream producing a gaseous product stream and a rich amine stream. Preferably, the $CO_2$ sweetening absorption zone is operated to reduce the $H_2S$ content to, for example, less than about 100 ppm in the $CO_2$ contained in the gaseous product stream while minimizing the $CO_2$ content of the acid gas removed, that is, achieving maximum $CO_2$ "slippage" through the $CO_2$ sweetening absorber.

Selective absorption of $H_2S$ in the $CO_2$ sweetening zone can be promoted by limited contact time, low temperature, and special mechanical tray design features.

The high selectivity of tertiary amines for $H_2S$ as compared with $CO_2$ is believed to arise because these amines lack labile hydrogen atoms and, hence, cannot react directly with $CO_2$ to form carbamate structures such as shown in (I) below:

$$CO_2 + 2[Amine] \rightleftharpoons [Amine]^+ + [Amine]-\overset{\overset{O}{\|}}{C}-O^- \quad (I)$$

Similarly, in DIPA which can be used according to the invention, the reaction with $CO_2$ to form stable carbamate structures is sterically hindered. Consequently, sterically hindered amines such as DIPA and tertiary amines must absorb $CO_2$ by the relatively slow acid-base reaction sequence such as shown in (II) below which is far slower than the carbamate mechanism (I):

$$CO_2 + H_2O \rightleftharpoons H_2CO_3$$

$$H_2CO_3 \rightleftharpoons H^+ + HCO_3^-$$

$$HCO_3^- \rightleftharpoons H^+ + CO_3^-$$

$$H^+ + [Amine] \rightleftharpoons [Amine]^+ \quad (II)$$

$H_2S$, on the other hand, reacts directly with tertiary and sterically hindered amines by very rapid proton transfer such as shown in (III) below:

$$H_2S + [Amine] \rightleftharpoons [Amine]^+ + HS^- \quad (III)$$

Thus, by selecting vapor liquid contact times so as to load the amine solution with $H_2S$ but not so long as to allow significant $CO_2$ absorption to occur, a high degree of selectivity for $H_2S$ can be attained. The $CO_2$ sweetening absorption step according to the invention will generally involve contacting the normally gaseous stream with the alkanolamine solutions in any suitable contacting vessel. In such processes, the normally gaseous mixture containing $H_2S$ and $CO_2$ from which the $H_2S$ is to be selectively removed may be brought into intimate contact with the absorption solution using conventional means, such as a tower or vessel containing suitable packing (e.g., rings or saddles), trays (e.g., sieve plates), or other suitable vapor liquid contact devices. Further, in the selective $H_2S$ absorption steps of the invention, special vapor-liquid contacting devices such as are known in the art can be used to enhance $H_2S$ selectivity.

According to the invention, the $CO_2$ sweetening absorption step can be conducted by feeding the normally gaseous mixture into the lower portion of the $CO_2$ sweetening absorber while lean alkanolamine solution is fed into the upper region of the absorber. A gaseous product stream freed largely from the $H_2S$, emerges from the upper portion of the tower, and a rich alkanolamine solution which contains the selectively absorbed $H_2S$ as well as some $CO_2$, leaves the tower near or at its bottom. Preferably, the inlet temperature of the alkanolamine solution during the absorption step is in the range of about 35° to about 60° C., and more preferably from about 40° to about 50° C. Pressures may vary widely; acceptable pressures are between 20 to 1000 psia, and preferably between 25 to 250 psia in the absorber. The contacting takes place under conditions such that the $H_2S$ is selectively absorbed by the solution. The absorption apparatus is designed so as to limit the residence time of the liquid in the absorber to minimize $CO_2$ pickup while at the same time maintaining sufficient contact of gas with liquid to absorb a maximum amount of $H_2S$. The amount of liquid required to be circulated to obtain a given degree of $H_2S$ removal will depend on the type and concentration of the amine and on the partial pressures of $H_2S$ and $CO_2$ in the feed gas.

A typical procedure for the $CO_2$ sweetening step of the process comprises selectively absorbing $H_2S$ via countercurrent contact of the gaseous mixture containing $H_2S$ and $CO_2$ with the aqueous alkanolamine solution in a column containing a plurality of trays at a moderate temperature, e.g., below 50° C., said tray column having fewer than 20 contacting trays, with e.g., 10 to 16 trays being typically employed.

After contacting the gaseous stream with the alkanolamine solution, which becomes saturated or partially saturated with $H_2S$, the rich alkanolamine solution is regenerated so that it may be recycled back to the $CO_2$ sweetening absorber. Regeneration or desorption of the acid gases from the rich alkanolamine solution can be accomplished by conventional means such as pressure reduction of the solution and increase of temperature. Preferably, the solution is sent to a vessel of similar construction to that used in the absorption step, at the upper portion of the vessel, and passing an inert stripping gas, preferably steam, upwardly through the vessel. The regenerated lean alkanolamine solution, after having at least a portion of the $H_2S$ removed therefrom can be recycled back to the absorbing vessel. Makeup absorbent may be added as needed.

In a preferred regeneration technique, the $H_2S$-rich amine solution from the $CO_2$ sweetening absorber can be sent to a regenerator wherein the absorbed $H_2S$ is stripped by steam which is generated by reboiling the solution. Preferably, the same regenerator can be used for regenerating the rich alkanolamine solutions from both the $CO_2$ sweetening absorber and the hydrocarbon sweetening absorber described in more detail below. Alternatively, of course, separate regenerators can be used. Pressure in the regenerator can be usually in the range of about 15 to 50 psia, preferably 20 to 30 psia. Stripper temperatures will, of course, depend on stripper pressure and amine concentration. The temperature can be typically in the range from about 100° to 130° C., preferably about 115° to 120° C. Heating of the solution to be regenerated may suitably be effected by means of indirect heating with steam. It is also possible, however, to use direct injection of steam.

In the bulk $CO_2$ removal zone of the invention, a gaseous stream containing major amounts of $CO_2$ can be processed. Bulk $CO_2$ removal can be conducted by feeding the gaseous stream into the lower portion of the bulk $CO_2$ removal absorber while fresh lean alkanolamine solution, or as hereinafter described, preferably semilean alkanolamine solution, can be fed to the upper region of the bulk $CO_2$ absorber. A gaseous product stream, largely freed of $CO_2$, can thus be produced from the upper region of the absorber and a second rich alkanolamine solution, which contains absorbed $CO_2$, and $H_2S$, can be removed from the tower near or at its bottom. The contacting takes place under conditions favoring removal of most of the $CO_2$ (for example, to less than about 5 to 10 mol% $CO_2$), i.e., high contact time and moderately high temperatures and pressures. Longer contact time favors $CO_2$ absorption as discussed above. As solution circulation rate decreases, pumping energy requirements decrease while net volumetric acid gas loading increases. Net volumetric acid gas loading is the volume of acid gas in the rich amine per unit volume of amine, minus the volume of acid gas in the lean amine per unit volume of amine. Reboiler energy requirements are directly dependent on the solution circulation rate and the regeneration temperature. Therefore, total energy consumption, which includes pumping and reboiler energy, is approximately minimized by maximizing the net volumetric acid gas loading of the alkanolamine. Thus, absorption and regeneration temperatures in the bulk $CO_2$ absorber are preferably set such that the volumetric acid gas loading is maximized. Mass transfer efficiency declines in both absorber and regenerator as temperature is reduced. Therefore, the optimum operating absorber and regenerator temperatures are generally somewhat higher than the theoretical optimum temperatures due to mass transfer efficiency limitations. In the preferred embodiment, the inlet temperature of the absorption solution during bulk $CO_2$ removal is approximately equal to the temperature in the bulk $CO_2$ absorber, and is in the range of about 60° to about 95° C., and more preferably from about 80° to about 90° C. Absorber pressures may vary widely; acceptable pressures are between 100 to 1000 psia, and most preferably with $CO_2$ partial pressures of 150 to 300 psia in feed to the bulk $CO_2$ removal absorber.

A typical procedure for the bulk $CO_2$ removal absorption step of the process comprises absorbing $CO_2$, and $H_2S$, via countercurrent contacting of a gaseous stream containing major amounts of $CO_2$ with an aqueous alkanolamine solution in an absorber having a plurality of trays at a temperature, in the range described above, said absorber having 15 to 30 trays, with, for example, 20 trays being typically used.

After contacting the gaseous stream, a rich alkanolamine solution stream is produced which is saturated or partially saturated with $CO_2$. The rich amine stream can be thoroughly regenerated with high energy consumption, for example, as described above in general terms for the $CO_2$ sweetening step, and recycled back to the bulk $CO_2$ removal absorber. Preferably, however, the regeneration can be accomplished with low energy consumption by an adiabatic, essentially atmospheric, flash regeneration procedure to yield a semilean alkanolamine solution which can be returned to the bulk $CO_2$ removal absorber. Various techniques can be advantageously used to increase efficiency, for example, a portion of the semilean alkanolamine solution withdrawn from the flash vessel can be fed to the lower region of the bulk $CO_2$ removal absorber without cooling while the remaining semilean alkanolamine solution can be cooled before being returned to the upper portion of the bulk $CO_2$ removal absorber. Such cooling of the solution can reduce the $CO_2$ partial pressure in the semilean solution and thereby can reduce the $CO_2$ content of the gaseous overhead product stream produced from the bulk $CO_2$ removal absorber. The cooled amine also cools the gaseous product stream before it enters the final hydrocarbon sweetening absorption zone where lower temperature favors $H_2S$ removal to a low level.

In the hydrocarbon sweetening zone of the invention, a gaseous stream from which major amounts of $CO_2$ and $H_2S$ have been removed, can be processed. The gaseous stream can be contacted with a well-stripped alkanolamine solution at lower temperature, 40°-50° C. A gaseous product stream comprising residue gas having less than, for example, about 4 ppm $H_2S$ with slippage of $CO_2$ allowed up to about 2 mol% $CO_2$ consistent with sales gas specifications can thus be produced as well as a third rich alkanolamine solution comprising absorbed $H_2S$ and $CO_2$.

Regeneration of the rich alkanolamine solution from the hydrocarbon sweetening absorber can be as described above for regeneration of the rich alkanolamine solution from the $CO_2$ sweetening absorption zone. According to a preferred embodiment, the rich alkanolamine solutions from the $CO_2$ sweetening absorber and from the final hydrocarbon sweetening absorber can be combined and regenerated in the same regeneration zone producing a single acid gas stream and a single lean alkanolamine stream. Alternatively, separate regenerators for the $CO_2$ sweetening and final hydrocarbon sweetening absorbers can be used. The lean amine circulation to the hydrocarbon sweetening absorber will typically be only about 1–10% of the total amine circulation since only a small portion of $H_2S$ and $CO_2$ remains in the feed to the final hydrocarbon sweetening absorber. The regenerated alkanolamine solution can pass through a lean-rich exchanger and can be further cooled before entering the final hydrocarbon sweetening absorber. This absorber is designed to ensure $H_2S$ and $CO_2$ removal consistent with specifications on the product gas. Moreover, $H_2S$ removal to meet the tight sales gas specification is enhanced in the final hydrocarbon sweetening absorber following the bulk $CO_2$ removal because of (1) reduced total solution loading and (2) increased fraction of the total loading is due to $H_2S$.

According to a preferred aspect of the invention, the bulk $CO_2$ removal absorber and the final hydrocarbon sweetening absorber can be combined in a single column. In this combination, the second gaseous product stream can be passed by a vapor path directly from the top of the bulk $CO_2$ removal absorber into the bottom region of the final hydrocarbon sweetening absorber. Separate columns can, of course, also be used. When a combined column is used, the rich amine from the final hydrocarbon sweetening absorber can be removed, for example, from a trapout tray just above the bulk $CO_2$ removal absorber. Alternatively, since the same alkanolamine solution is being utilized for both the hydrocarbon sweetening and bulk $CO_2$ removal zones, the rich amine stream from the final hydrocarbon sweetening absorber can be allowed to flow through the bulk $CO_2$ removal absorber to be further loaded with $CO_2$ before being withdrawn in admixture with the rich amine stream from the bulk $CO_2$ removal absorber.

As indicated above, during regeneration of the rich alkanolamine stream from the $CO_2$ sweetening absorption zone, an acid gas stream can be produced comprising predominantly $CO_2$ and $H_2S$. The acid gas produced by this regeneration will be concentrated in $H_2S$ as compared with the $H_2S$ content in the gaseous feed to the invented process. For certain applications, if the acid gas stream from regeneration contains less than about 10–15 mol% $H_2S$, a further selective $H_2S$ absorption stage can advantageously be used to further concentrate the $H_2S$ in the acid gas and to recover additional high purity $CO_2$ for other purposes.

Figure 3:
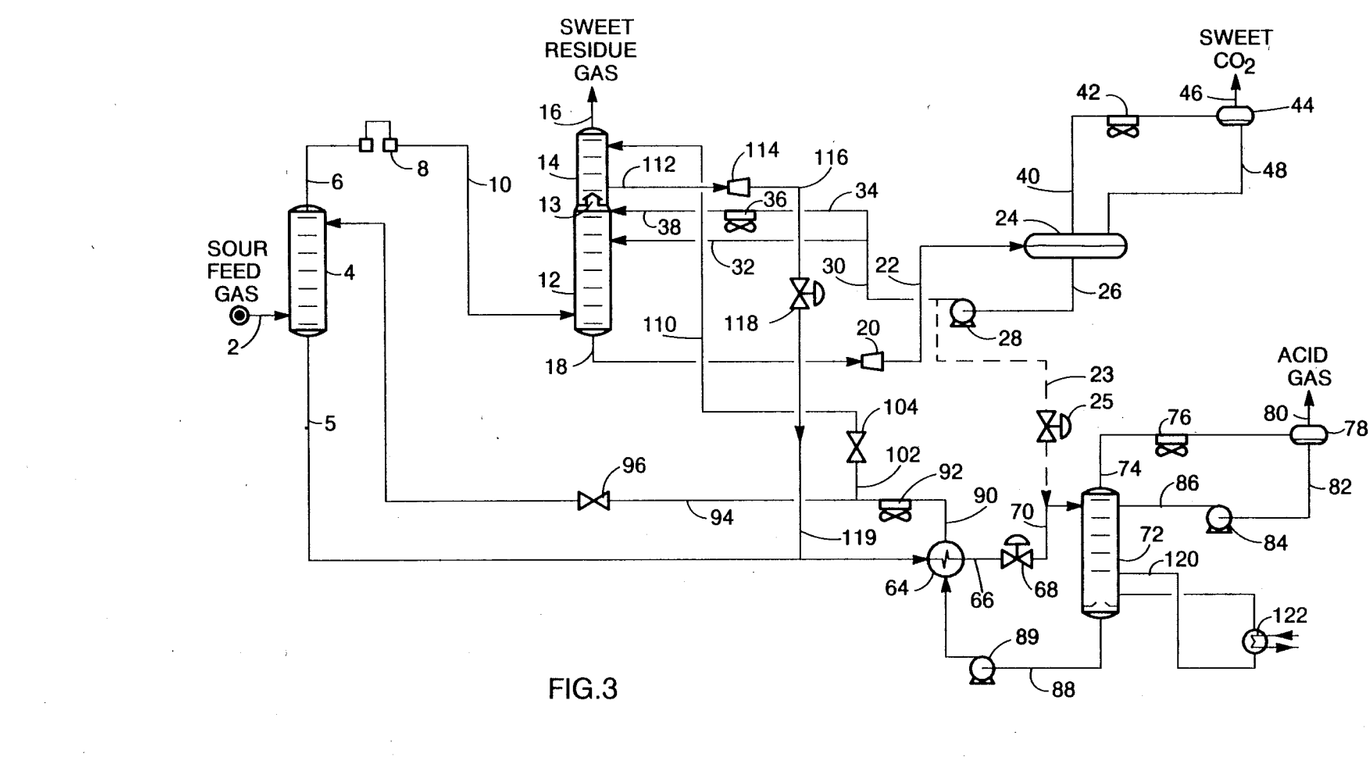
FIG. 3 illustrates schematically the first embodiment of the invention.

The invention will be better understood and appreciated from the following detailed description of the drawings in which FIG. 3 represents schematically the first embodiment of the invention according to FIG. 1, utilizing a $CO_2$ sweetening absorber, a bulk $CO_2$ removal absorber, and a final hydrocarbon sweetening absorber, in sequence, to produce a residue gas having, for example, less than 4 ppm $H_2S$ and less than about 2 mol% carbon dioxide, as well as a sweet $CO_2$ product stream having less than about 100 ppm $H_2S$ and an acid gas stream enriched in $H_2S$ content.

Referring now to FIG. 3 in detail, a sour gaseous feed stream comprising 49 mol% carbon dioxide, 1 mol% hydrogen sulfide, and the remainder consisting of hydrocarbons such as methane, ethane, propane, and the like can be introduced by line 2 into the lower region of $CO_2$ sweetening absorber 4 and a lean alkanolamine solution, for example, MDEA or the like, can be introduced in an upper region via line 94 and flow control valve 96. The $CO_2$ sweetening absorber 4 can be operated under conditions effective for selective $H_2S$ removal as hereinabove described and the first gaseous product stream from which a substantial portion of $H_2S$ has been removed can be removed by line 6, compressor 8, and line 10, and introduced into the lower region of the bulk $CO_2$ removal absorber 12. When the sour feed gas is available at suitably high pressure, the compressor 8 will, of course, not be required.

In the bulk $CO_2$ removal absorber 12, the gaseous product stream provided by line 10 comprising predominantly hydrocarbons and carbon dioxide can be contacted with a semilean alkanolamine solution introduced at one or more points, for example, via lines 32 and 38, and carbon dioxide can be removed, for example, to less than about 5 to 10 mol% carbon dioxide. The second gaseous product stream from which the bulk of the carbon dioxide has been removed can then be passed overhead by vapor path 13 into the lower region of a final hydrocarbon sweetening absorber 14, which in the illustrated embodiment is combined in a single column with the bulk $CO_2$ removal absorber 12. Separate columns can, of course, also be utilized.

In the final hydrocarbon sweetening absorber 14, a lean alkanolamine solution can be introduced by line 110 into an upper portion, contacting and removing substantially all of the remaining hydrogen sulfide from the gaseous product stream introduced by vapor path 13 and producing a sweet gaseous product stream (residue gas stream) containing essentially all of the hydrocarbons and, for example, less than about 4 ppm hydrogen sulfide and less than about 2 mol% carbon dioxide, which can be removed by line 16.

The first rich alkanolamine solution can be removed from the $CO_2$ sweetening absorber 4 near the bottom thereof by line 5, passed in heat exchange relationship with lean amine from stripper column 72 in lean/rich exchanger 64, then by line 66, valve 68, and line 70 into an upper portion of stripper column 72. In stripper column 72, heat can be provided for generation of stripping vapor by removing liquid by line 120 to reboiler 122 and returning the heated liquid and vapor to the column. $H_2S$ and $CO_2$ desorbed from the rich alkanolamine solution in column 72 can be removed overhead by line 74, condenser 76, separator 78, and the acid gas overhead passed, for example, to a Claus sulfur recovery unit by line 80, or to an additional stage of selective $H_2S$ removal (not shown) for further concentrating the $H_2S$ in the feed for a Claus plant. Condensed aqueous liquid can be returned to the top region of column 72 from separator 78 by line 82, reflux pump 84, and line 86.

Lean, regenerated alkanolamine solution can be removed from the bottom of $H_2S$ stripper 72 by line 88, pump 89, cooled in lean/rich exchanger 64 in heat exchange relationship with the rich alkanolamine solution from $CO_2$ sweetening absorber 4, then passed by line 90, cooler 92, line 94, and flow control valve 96 to the upper portion of $CO_2$ sweetening absorber 4.

A rich alkanolamine solution can also be removed from final hydrocarbon sweetening absorber 14 near the bottom thereof, for example, by line 112, power recovery turbine 114, line 116, control valve 118, line 119 and combined with the rich alkanolamine solution from the $CO_2$ sweetening absorber in line 5, and thereafter treated as described above. Alternatively, when rich amine from the final hydrocarbon sweetening absorber is not trapped out, but is allowed to flow down into the bulk $CO_2$ removal section 12, a portion of the semilean amine from pump 28, (described in greater detail below) can be diverted via line 23 and valve 25 to line 70. Following regeneration, a portion of the lean amine in line 94 can be returned to the final hydrocarbon sweetening absorber 14, for example, by line 102, flow control valve 104, and line 110 to the upper region of the final hydrocarbon sweetening absorber 14.

It will be appreciated that although in the illustrated embodiment of FIG. 3, the rich alkanolamine solutions from the $CO_2$ sweetening absorber 4 and the final hydrocarbon sweetening absorber 14 are regenerated in a single $H_2S$ desorber 72, it is also possible and in accordance with the invention to use separate $H_2S$ desorbers for separate regeneration of each of these streams.

The rich alkanolamine solution from bulk $CO_2$ removal absorber 12 can be removed for regeneration, for example, by line 18, power recovery turbine 20, and provided by line 22 to $CO_2$ flash vessel 24. The heat necessary to sustain solution temperature can, if desired, be introduced into the flash vessel by a heater on the rich solution. Vapor can be removed from the flash vessel by line 40, cooled in condenser 42, and provided to separator 44. A sweet $CO_2$ stream having less than about 100 ppm $H_2S$ can be removed by line 46 from separator 44. The aqueous liquid from separator 44 can be returned to the flash vessel 24 by line 48. The semilean flashed amine solution can be removed from flash vessel 24 via line 26, pump 28 and line 30. A portion of the semilean amine solution in line 30 can be sent to cooler 36 by line 34, and can then be introduced by line 38 at the top of bulk $CO_2$ absorber 12.

Figure 4:
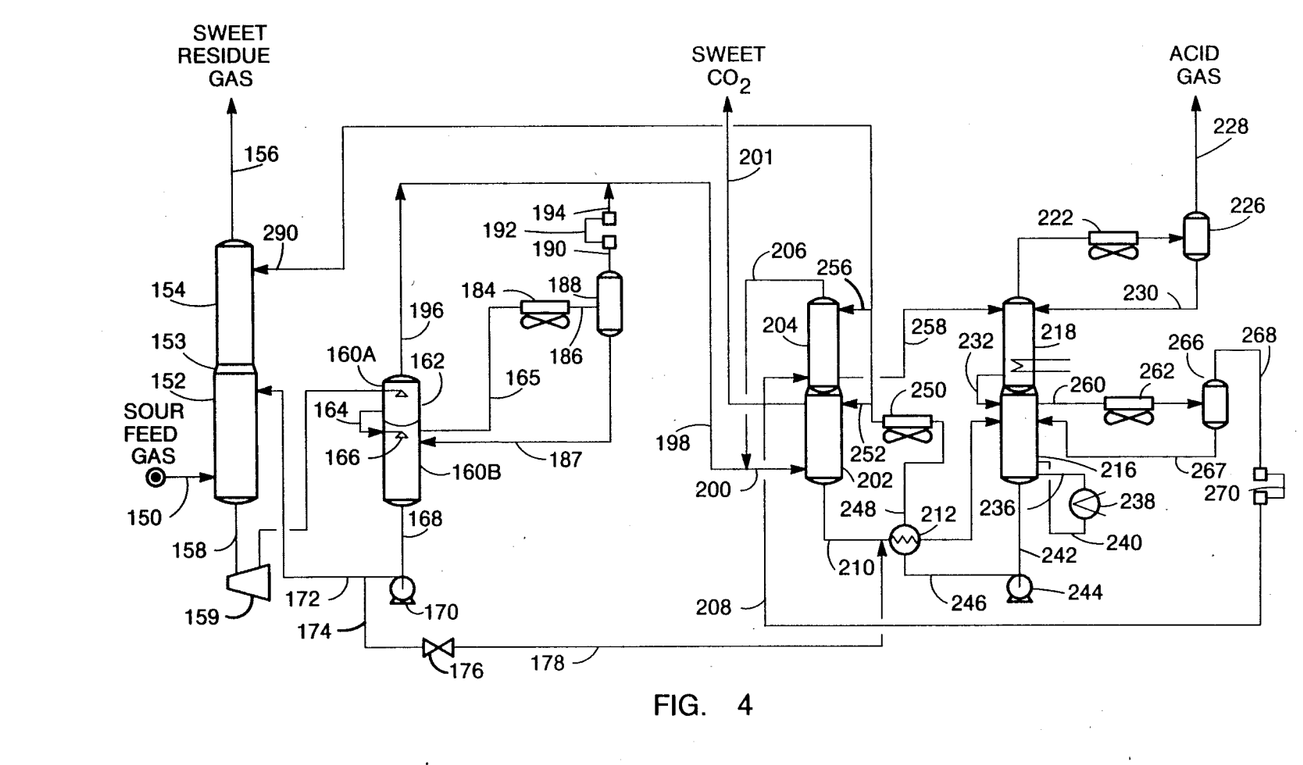
FIG. 4 illustrates schematically the second embodiment of the invention.

FIG. 4 represents schematically the (second) embodiment of the invention according to FIG. 2 utilizing a bulk $CO_2$ removal absorber and a final hydrocarbon sweetening absorber in sequence to produce a residue gas having, for example, less than about 4 ppm $H_2S$ and less than about 2 mol percent $CO_2$; and further utilizes a $CO_2$ sweetening absorber on the sour $CO_2$ removed in the bulk $CO_2$ removal step to produce a sweet $CO_2$ product stream having less than about 100 ppm $H_2S$ and an acid gas stream enriched in $H_2S$ content. Also illustrated in FIG. 4 is the aspect of the invention according to which the sour $CO_2$ stream can be passed through an additional $H_2S$ selective absorption zone operated to produce an acid gas feed to a Claus Plant having greater than about 10-15 mol percent hydrogen sulfide.

Referring now to FIG. 4 in more detail, a sour gaseous feed stream comprising 90% $CO_2$ with a relatively low $H_2S$ content (0.2 mol% in the $CO_2$), and hydrocarbons can be introduced by line 150 into the bottom section 152 of vessel 153 operated for bulk $CO_2$ removal absorption. A semilean alkanolamine solution, such as, for example, MDEA, can be introduced by line 172 into the upper region of the bottom section 152 of vessel 153 under conditions as described above effective for absorption of at least a substantial portion of the $CO_2$ from the gaseous feedstream. The gaseous vapors from which a substantial portion of $CO_2$ and $H_2S$ have been removed then rise into top section 154 of vessel 153 operated as a final hydrocarbon sweetening absorber, and lean alkanolamine solution can be introduced in the upper region of section 154, for example, by line 290, further removing $H_2S$ and $CO_2$ from the rising vapors, thereby producing a residue gas stream which can be removed by line 156 having, for example, less than about 2 mol% carbon dioxide and less than about 4 ppm $H_2S$.

Rich alkanolamine solution can be removed from the bottom of vessel 152, for example, by line 158 and power recovery turbine 159, and introduced into the upper stage of, for example, a two-stage flash $CO_2$ desorber having upper and lower stages 160A and 160B, respectively. In the first stage desorber 160A, the rich alkanolamine solution can be flashed at intermediate pressure, preferably with atomization by nozzles 162 and a substantial amount of $CO_2$ desorbed and removed by line 196. Liquid can be removed from the bottom of upper stage 160A by line 164 and introduced into the upper portion of lower pressure stage 160B again by flashing preferably with atomization by nozzles 166. Gases desorbed in the lower stage 160B can then be removed by line 165. Regenerated semilean alkanolamine can be removed from the bottom of $CO_2$ desorber 160B by line 168, and returned to bulk $CO_2$ removal absorber 152 by pump 170, and line 172.

A portion of the regenerated semilean solution removed from the base of $CO_2$ desorber 160B can be taken from line 172 by line 174, control valve 176, and line 178 and combined with rich amine in line 210 leaving the first stage selective $H_2S$ absorber 202, passed through heat exchanger 212 and introduced into stripper column 216. $CO_2$ and $H_2S$ in the combined amine stream can be desorbed in stripper column 216. The lean amine leaving the base of column 216 by line 242, pump 244, and line 246, after heat exchange in exchanger 212 can be passed by line 248 for cooling in air cooler 250. A portion of the cooled lean amine is drawn off via line 290 and returned to the hydrocarbon sweetening absorber 154. The balance is sent to the selective $H_2S$ removal absorbers via lines 252 and 256.

Desorbed acid gas removed from the low pressure desorber 160B by line 165 can be cooled in condenser 184 and provided by line 186 to separator 188. Aqueous condensate from the separator 188 can be returned to desorber 160 B by line 187. Acid gas removed from the separator 188 in line 190 can then be provided by compressor 192 and line 194 to be combined in line 198 with the $CO_2$ gaseous stream from the first stage desorber 160A in line 196.

The combined acid gas stream in line 198 from the two stage $CO_2$ desorber can be provided by line 200 to the lower region of a first $CO_2$ sweetening absorber 202. Lean alkanolamine solution can be introduced in an upper portion thereof, for example, by line 252, and $H_2S$ can be selectively removed as described above from the ascending gases. Ascending gas from which $H_2S$ has been removed can then be produced as a sweet $CO_2$ product stream removed by line 201. A recycle stream comprising $CO_2$ and $H_2S$ can be removed from the upper portion of the pre-Claus $H_2S$ selective absorber 204, also described below, by line 206 and recycled to the inlet of the $CO_2$ sweetening absorber 202 by lines 206 and 200.

Rich alkanolamine solution can be removed from the bottom of the $CO_2$ sweetening absorber 202, for example, by line 210, combined with semilean amine slipstream from line 178, and provided via lean/rich exchanger 212 to stripper column 216. In stripper 216, $H_2S$ and $CO_2$ are desorbed from the rich alkanolamine solution, for example, by steam stripping, with heat being introduced by removing liquid via line 240, heating in reboiler 238, and returning heated liquid and vapor by line 236. Lean alkanolamine solution from the bottom of stripper 216 can then be returned to the $CO_2$ sweetening absorber 202 and the pre-Claus $H_2S$ selective absorber 204 by line 242, pump 244, line 246, lean/rich exchanger 212, line 248, cooler 250, and lines 252 and 256, respectively. Desorbed gases can be removed from the upper portion of stripper column 216, for example, by line 260, condenser 262, and provided to separator 266. Condensed liquids can be returned to the desorber 216 by line 267.

Lean acid gas containing only about 0.2% $H_2S$ can be removed from the separator 266 by line 268 and enriched by pre-Claus $H_2S$ selective absorption. The acid gas can then be introduced by compressor 270 and line 208 into the lower portion of pre-Claus $H_2S$ selective absorber 204 having lean alkanolamine solution introduced in the upper region thereof by line 256. A rich alkanolamine solution can be removed from the bottom of selective absorber 204 by line 258 and provided to the pre-Claus $H_2S$ desorber 218 located in a column section above the stripper 216. In pre-Claus $H_2S$ desorber 218, $H_2S$ and $CO_2$ are desorbed from the rich alkanolamine solution, for example, by steam stripping. Gases removed from pre-Claus $H_2S$ desorber 218 can be provided by condenser 222 to separator 226. Condensate can be returned from separator 226 to the desorber by line 230. An enriched acid gas containing about 32 mol% hydrogen sulfide and suitable for Claus sulfur recovery can be removed by line 228. Alkanolamine solution can be removed from the bottom of pre-Claus $H_2S$ desorber 218 and provided by line 232 into the upper portion of $CO_2$ sweetening stripper 216 for further stripping as described above.

The invention will be further understood and appreciated from the following examples in which EXAMPLE 1 illustrates stream compositions and conditions according to the embodiment of FIG. 3 and EXAMPLE 2 illustrates stream compositions and conditions according to the embodiment of FIG. 4.

EXAMPLE I

TABLE 1

| Stream Number | Vapor Rate - mols/hr | | | | Temp. (°F.) | Press. (psia) | Amine (gpm) |
|---|---|---|---|---|---|---|---|
| | $CO_2$ | $H_2S$ | HC | Total | | | |
| 2 | 931 | 19.0 | 950 | 1900 | 100 | 50 | — |
| 5 | — | — | — | — | 130 | 50 | 220 |
| 6 | 826 | 0.07 | 949 | 1775 | 114 | 46 | — |
| 13 | 208 | 0.01 | 948 | 1182 | 182 | 296 | — |
| 16 | 19 | 0.00 | 946 | 965 | 131 | 292 | — |
| 18 | — | — | — | — | 199 | 300 | 1500 |
| 30 | — | — | — | — | 180 | 316 | 1500 |
| 32 | — | — | — | — | 180 | 316 | 750 |
| 33 | — | — | — | — | 120 | 312 | 750 |
| 46 | 618 | 0.06 | 1 | 619 | 180 | 23 | — |
| 80 | 294 | 18.9 | 3 | 316 | 110 | 23 | — |
| 88 | — | — | — | — | 245 | 28 | 670 |
| 94 | — | — | — | — | 120 | 300 | 220 |
| 102 | — | — | — | — | 120 | 300 | 450 |
| 112 | — | — | — | — | 159 | 292 | 450 |

[1] Columns 4, 12, 14, and 72 are modeled as having 16, 17, 20 and 20 trays, respectively; 50 wt % MDEA is used as absorption solution.

EXAMPLE II

TABLE 2

| Stream Number | Vapor Rate - mols/hr | | | | Temp. (°F.) | Press. (psia) | Amine (gpm) |
|---|---|---|---|---|---|---|---|
| | $CO_2$ | $H_2S$ | HC | Total | | | |
| 150 | 8695 | 17 | 950 | 9662 | 120 | 310 | |
| 156 | 10 | 3 ppm | 860 | 870 | | 300 | |
| 158 | | | | | 187 | 300 | |
| 172 | | | | | 160 | 330 | 11000 |
| 196 | 4340 | 9 | 50 | 4399 | 165 | 80 | |
| 198 | 8685 | 17 | 90 | 8792 | 120 | 80 | |
| 201 | 8651 | 0.7 | 90 | 8742 | 120 | 80 | |
| 208 | 560 | 1 | 6 | 567 | 120 | 85 | |
| 228 | 34 | 16.3 | 0.5 | 51 | 120 | 25 | |
| 246 | | | | | 252 | 130 | 3100 |
| 252 | | | | | 120 | 90 | 300 |
| 256 | | | | | 120 | 90 | 2800 |
| 290 | | | | | 120 | 330 | 150 |

[1] Columns 152, 154, 180, 202, 204, 216, and 218 are modeled as having 30, 16, 20, 16, 16, 20, and 20 trays respectively; 35 wt % MDEA is used as absorption solution.

It will be appreciated that there has been described a process for treating low quality gases which can achieve the following. First, the combination of $CO_2$ sweetening absorption and bulk $CO_2$ removal absorption according to the embodiment of FIG. 1 can produce a sweet $CO_2$ stream, containing less than, for example, 100 ppm $H_2S$. Such a sweet $CO_2$ stream meets current environmental requirements for pipelining and is suitable for reinjection into $CO_2$ miscible flood produced reservoirs or for other use. Secondly, by utilizing both a $CO_2$ sweetening and a bulk $CO_2$ removal absorption step prior to the final hydrocarbon sweetening absorption step, the amount of $H_2S$ and $CO_2$ ultimately reaching the final hydrocarbon sweetening absorption zone is greatly reduced, allowing the $H_2S$ and $CO_2$ specification of the hydrocarbon residue gas to be easily met with relatively low amine circulation and low energy input. Thirdly, the $CO_2$ sweetening absorption step concentrates $H_2S$ in the acid gas removed to provide a suitable feed to a sulfur recovery plant.

Further, it will be appreciated that a process has been described which accomplishes the following. First, by utilizing a single amine solution to accomplish all of the several absorption steps described heretofore; it becomes possible to consolidate equipment with resultant simplification of the process and associated reductions in investment and operating costs. For example, the bulk $CO_2$ removal and hydrocarbon sweetening steps can be accomplished in a single absorption column. Further, the lean amine used for selective $CO_2$ sweetening and for hydrocarbon sweetening can be provided by stripping in a single column. The use of a single amine solution also reduces the cost of solution inventory and eliminates the problem of solution intermingling with savings in equipment required to segregate solutions.

While the invention has been described as required in terms of preferred embodiments and giving specific operating ranges and conditions, it is to be understood that the invention is not limited thereby, but by the claims appended hereto.

What is claimed is:

1. Process for the removal of hydrogen sulfide and carbon dioxide from a gaseous feedstream comprising hydrocarbons comprising:

introducing the gaseous feedstream into a $CO_2$ sweetening absorption zone and contacting the gaseous feedstream with a first lean amine solution stream under conditions selective for the removal of hydrogen sulfide relative to carbon dioxide and absorbing at least a major portion of the hydrogen sulfide from the gaseous feedstream producing a first gaseous product stream and a first rich amine stream containing absorbed hydrogen sulfide;

introducing the first gaseous product stream into a bulk $CO_2$ removal absorption zone and contacting the first gaseous product stream with a second lean (or semilean) amine solution stream under conditions effective for absorbing and removing a major portion of carbon dioxide from the first gaseous product stream and producing a second gaseous product stream and a second rich amine stream containing absorbed carbon dioxide; and introducing the second gaseous product stream into a hydrocarbon sweetening absorption zone and contacting the second gaseous product stream with a third lean amine solution stream under conditions effective for removal of a major portion of all remaining carbon dioxide and hydrogen sulfide and producing a fourth gaseous product stream comprising hydrocarbons and a third rich amine stream, wherein the first lean amine solution, the second lean (or semilean) amine solution, and the third lean amine solution each comprises an amine selected from the group consisting of tertiary amines and sterically hindered amines.

2. Process as in claim 1 wherein:

each of the first lean amine solution, the second lean (or semilean) amine solution, and the third lean amine solution, are substantially identical.

3. Process as in claim 2 further comprising:

introducing the first rich amine stream and the third rich amine stream into a first regeneration zone and removing absorbed carbon dioxide and hydrogen sulfide therefrom and producing an acid gas stream, the first lean amine solution stream and the third lean amine solution stream;

introducing the second rich amine stream into a second regeneration zone and removing absorbed carbon dioxide therefrom and producing a $CO_2$ product stream lean in hydrogen sulfide and the second lean (or semilean) amine stream.

4. Process as in claim 3 further comprising:

introducing the acid gas stream into a pre-Claus selective $H_2S$ removal zone and producing a first gaseous stream enriched in $H_2S$ and a second gaseous stream enriched in $CO_2$.

5. Process as in claim 4 comprising:

introducing the first gaseous stream enriched in $H_2S$ into a second pre-Claus selective $H_2S$ removal zone and producing a third gaseous stream enriched in $H_2S$ and a fourth gaseous stream enriched in $CO_2$.

6. Process as in claim 4 comprising:

introducing the second gaseous stream enriched in $CO_2$ to the feed to the $CO_2$ sweetening zone;

returning the fourth gaseous stream enriched in $CO_2$ to the first pre-Claus selective $H_2S$ removal zone;

7. Process for the removal of $H_2S$ and $CO_2$ from a gaseous feedstream comprising:

(a) introducing the gaseous feedstream into a bulk $CO_2$ removal absorption zone and contacting the gaseous feedstream with a first lean (or semilean) amine solution stream under conditions effective for absorbing and removing a major portion of carbon dioxide and a first portion of hydrogen sulfide from the gaseous feedstream and producing a first gaseous product stream and a first rich amine stream containing absorbed carbon dioxide and hydrogen sulfide;

(b) introducing the first gaseous product stream into a hydrocarbon sweetening absorption zone and contacting the first gaseous product stream with a second lean amine solution stream under conditions effective for removal of a major portion of the remaining hydrogen sulfide and producing a second gaseous product stream comprising predominantly hydrocarbons, and a second rich amine stream;

(c) removing absorbed carbon dioxide and hydrogen sulfide from the first rich amine stream and the second rich amine stream and producing a first acid gas stream containing such removed carbon dioxide and hydrogen sulfide;

(d) introducing the first acid gas stream into a $CO_2$ sweetening absorption zone and contacting the acid gas stream with a third lean amine solution stream under conditions selective for the removal of hydrogen sulfide relative to carbon dioxide and absorbing at least a major portion of the hydrogen sulfide from the acid gas stream producing a third gaseous product stream comprising predominately carbon dioxide and a third rich amine stream containing absorbed hydrogen sulfide; and (e) removing absorbed hydrogen sulfide from the third rich amine stream and producing a second acid gas stream containing such removed hydrogen sulfide, and the third lean amine stream, wherein (f) the first lean (or semilean) amine solution, the second lean amine solution, and the third lean amine solution each comprises an amine selected from the group consisting of tertiary amines and sterically hindered amines effective for selective removal of hydrogen sulfide relative to carbon dioxide.

8. Process as in claim 7 wherein:

the first lean (or semilean) amine solution, the second lean amine solution and the third lean amine solution are substantially identical.

9. Process as in claim 8 wherein step (c) of claim 7 comprises:

introducing the first rich amine stream and the second rich amine stream into a first regeneration zone and removing absorbed carbon dioxide and hydrogen sulfide therefrom and producing a first acid gas stream, and the first lean (or semilean) amine solution stream, introducing the third rich amine stream and a portion of the first lean (or semilean) amine stream, essentially equal in volume to the second lean amine stream, into a second regeneration zone, producing a second acid gas stream enriched in hydrogen sulfide, the second lean amine stream, and the third lean amine stream.

10. Process as in claim 7 further comprising:

introducing the second acid gas stream into a pre-Claus selective $H_2S$ removal zone and producing a third acid gas stream enriched in $H_2S$ and a gaseous stream comprising primarily $CO_2$.

11. Process as in claim 10 further comprising:

combining the gaseous stream comprising primarily $CO_2$ with the first acid gas stream, and contacting the thus combined stream with the third lean amine solution under conditions selective for the removal of hydrogen sulfide relative to carbon dioxide.

* * * * *